(12) United States Patent  
Wang et al.

(10) Patent No.: US 7,769,492 B2
(45) Date of Patent: Aug. 3, 2010

(54) GRAPHICAL INTERFACE FOR A REMOTE PRESENCE SYSTEM

(75) Inventors: Yulun Wang, Goleta, CA (US); Charles S. Jordan, Santa Barbara, CA (US); Marco Pinter, Santa Barbara, CA (US); Greg Brallier, Santa Barbara, CA (US); Jon Mears, Plano, TX (US)

(73) Assignee: InTouch Technologies, Inc., Goleta, CA (US)

( * ) Notice: Subject to any disclaimer, the term of this patent is extended or adjusted under 35 U.S.C. 154(b) by 1000 days.

(21) Appl. No.: 11/360,235

(22) Filed: Feb. 22, 2006

(65) Prior Publication Data

US 2007/0198130 A1     Aug. 23, 2007

(51) Int. Cl.
*G05B 19/04* (2006.01)

(52) U.S. Cl. ..................................... 700/257
(58) Field of Classification Search ................. 700/245, 700/257, 259, 262
See application file for complete search history.

(56) References Cited

U.S. PATENT DOCUMENTS

| | | | |
|---|---|---|---|
| 3,821,995 A | 7/1974 | Aghnides | |
| 4,413,693 A | 11/1983 | Derby | |
| 4,471,354 A | 9/1984 | Smith | |
| 4,519,466 A | 5/1985 | Shiraishi | |
| 4,638,445 A | 1/1987 | Mattaboni | |
| 4,709,265 A | 11/1987 | Silverman et al. | |
| 4,733,737 A | 3/1988 | Falamak | |
| 4,803,625 A | 2/1989 | Fu et al. | |
| 4,875,172 A | 10/1989 | Kanayama | |
| 4,977,971 A | 12/1990 | Crane, III et al. | |
| 5,073,749 A | 12/1991 | Kanayama | |
| 5,084,828 A | 1/1992 | Kaufman et al. | |
| 5,130,794 A | 7/1992 | Ritchey | |
| 5,186,270 A | 2/1993 | West | |
| 5,305,427 A | 4/1994 | Nagata | |
| 5,341,242 A | 8/1994 | Gilboa et al. | |
| 5,341,457 A | 8/1994 | Hall, II et al. | |
| 5,341,854 A | 8/1994 | Zezulka et al. | |
| 5,374,879 A | 12/1994 | Pin et al. | |
| 5,419,008 A | 5/1995 | West | |
| 5,441,047 A | 8/1995 | David et al. | |
| 5,462,051 A | 10/1995 | Oka et al. | |
| 5,486,853 A | 1/1996 | Baxter et al. | |

(Continued)

FOREIGN PATENT DOCUMENTS

CA     2289697 A1     11/1998

(Continued)

OTHER PUBLICATIONS

F. Ando et al., "A Multimedia Self-service Terminal with Conferencing Functions", 1995, IEEE, pp. 357-362.

(Continued)

*Primary Examiner*—Kim T Nguyen
(74) *Attorney, Agent, or Firm*—Ben J. Yorks; Irell & Manella LLP

(57) ABSTRACT

A robot system that includes a mobile robot and a portable control station that communicate through a cellular network. Utilizing a cellular network allows the control station to be a portable device such as a laptop computer or a personal digital assistant.

20 Claims, 7 Drawing Sheets

U.S. PATENT DOCUMENTS

| | | | |
|---|---|---|---|
| 5,510,832 A | 4/1996 | Garcia | |
| 5,544,649 A | 8/1996 | David et al. | |
| 5,553,609 A | 9/1996 | Chen et al. | |
| 5,572,229 A | 11/1996 | Fisher | |
| 5,630,566 A | 5/1997 | Case | |
| 5,636,218 A | 6/1997 | Ishikawa et al. | |
| 5,701,904 A | 12/1997 | Simmons et al. | |
| 5,762,458 A | 6/1998 | Wang et al. | |
| 5,786,846 A | 7/1998 | Hiroaki | |
| 5,802,494 A | 9/1998 | Kuno | |
| 5,836,872 A | 11/1998 | Kenet et al. | |
| 5,838,575 A | 11/1998 | Lion | |
| 5,857,534 A | 1/1999 | DeVault et al. | |
| 5,871,451 A | 2/1999 | Unger et al. | |
| 5,917,958 A | 6/1999 | Nunally et al. | |
| 5,959,423 A | 9/1999 | Nakanishi et al. | |
| 5,966,130 A | 10/1999 | Benman, Jr. | |
| 6,006,946 A | 12/1999 | Williams et al. | |
| 6,036,812 A | 3/2000 | Williams et al. | |
| 6,133,944 A | 10/2000 | Braun et al. | |
| 6,135,228 A | 10/2000 | Asada et al. | |
| 6,170,929 B1 | 1/2001 | Wilson et al. | |
| 6,211,903 B1 | 4/2001 | Bullister | |
| 6,219,587 B1 | 4/2001 | Ahlin et al. | |
| 6,232,735 B1 | 5/2001 | Baba et al. | |
| 6,233,504 B1 | 5/2001 | Das et al. | |
| 6,233,735 B1 | 5/2001 | Ebihara | |
| 6,259,806 B1 | 7/2001 | Green | |
| 6,292,713 B1 | 9/2001 | Jouppi et al. | |
| 6,304,050 B1 | 10/2001 | Skaar et al. | |
| 6,325,756 B1 | 12/2001 | Webb et al. | |
| 6,346,950 B1 | 2/2002 | Jouppi | |
| 6,369,847 B1 | 4/2002 | James et al. | |
| 6,430,471 B1 | 8/2002 | Kintou et al. | |
| 6,430,475 B2 | 8/2002 | Okamoto et al. | |
| 6,438,457 B1 | 8/2002 | Yokoo et al. | |
| 6,463,361 B1 | 10/2002 | Wang et al. | |
| 6,474,434 B1 | 11/2002 | Bech | |
| 6,491,701 B2 | 12/2002 | Tierney et al. | |
| 6,496,099 B2 | 12/2002 | Wang et al. | |
| 6,507,773 B2 | 1/2003 | Parker et al. | |
| 6,522,906 B1 | 2/2003 | Salisbury et al. | |
| 6,532,404 B2 | 3/2003 | Colens | |
| 6,535,182 B2 | 3/2003 | Stanton | |
| 6,535,793 B2 | 3/2003 | Allard | |
| 6,543,899 B2 | 4/2003 | Covannon et al. | |
| 6,549,215 B2 | 4/2003 | Jouppi | |
| 6,581,798 B2 | 6/2003 | Liff et al. | |
| 6,587,750 B2 | 7/2003 | Gerbi et al. | |
| 6,594,552 B1 | 7/2003 | Nowlin et al. | |
| 6,646,677 B2 | 11/2003 | Noro et al. | |
| 6,666,374 B1 | 12/2003 | Green et al. | |
| 6,684,129 B2 | 1/2004 | Salisbury et al. | |
| 6,799,065 B1 | 9/2004 | Niemeyer | |
| 6,799,088 B2 | 9/2004 | Wang et al. | |
| 6,804,656 B1 | 10/2004 | Rosenfeld et al. | |
| 6,836,703 B2 | 12/2004 | Wang et al. | |
| 6,839,612 B2 | 1/2005 | Sanchez et al. | |
| 6,840,904 B2 | 1/2005 | Goldberg | |
| 6,845,297 B2 | 1/2005 | Allard | |
| 6,852,107 B2 | 2/2005 | Wang et al. | |
| 6,871,117 B2 | 3/2005 | Wang et al. | |
| 6,879,879 B2 | 4/2005 | Jouppi et al. | |
| 6,892,112 B2 | 5/2005 | Wang et al. | |
| 6,914,622 B1 | 7/2005 | Smith et al. | |
| 6,925,357 B2 | 8/2005 | Wang et al. | |
| 6,995,664 B1 | 2/2006 | Darling | |
| RE39,080 E | 4/2006 | Johnston | |
| 7,115,102 B2 | 10/2006 | Abbruscato | |
| 7,123,285 B2 | 10/2006 | Smith et al. | |
| 7,154,526 B2 | 12/2006 | Foote et al. | |
| 7,156,809 B2 | 1/2007 | Quy | |
| 7,161,322 B2 | 1/2007 | Wang et al. | |
| 7,164,969 B2 | 1/2007 | Wang et al. | |
| 7,174,238 B1 | 2/2007 | Zweig | |
| 2001/0037163 A1 | 11/2001 | Allard | |
| 2001/0054071 A1 | 12/2001 | Loeb | |
| 2002/0027597 A1 | 3/2002 | Sachau | |
| 2002/0057279 A1 | 5/2002 | Jouppi | |
| 2002/0058929 A1 | 5/2002 | Green | |
| 2002/0063726 A1 | 5/2002 | Jouppi | |
| 2002/0098879 A1* | 7/2002 | Rheey | 463/1 |
| 2002/0120362 A1 | 8/2002 | Lathan et al. | |
| 2002/0130950 A1 | 9/2002 | James et al. | |
| 2002/0141595 A1 | 10/2002 | Jouppi | |
| 2002/0183894 A1 | 12/2002 | Wang et al. | |
| 2003/0048481 A1 | 3/2003 | Kobayashi | |
| 2003/0050733 A1 | 3/2003 | Wang et al. | |
| 2003/0060808 A1 | 3/2003 | Wilk | |
| 2003/0100892 A1 | 5/2003 | Morley et al. | |
| 2003/0114962 A1 | 6/2003 | Niemeyer | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0151658 A1 | 8/2003 | Smith | |
| 2003/0220541 A1 | 11/2003 | Salisbury et al. | |
| 2004/0019406 A1 | 1/2004 | Wang et al. | |
| 2004/0088077 A1 | 5/2004 | Jouppi et al. | |
| 2004/0117065 A1 | 6/2004 | Wang et al. | |
| 2004/0143421 A1 | 7/2004 | Wang et al. | |
| 2004/0162637 A1 | 8/2004 | Wang et al. | |
| 2004/0167666 A1 | 8/2004 | Wang et al. | |
| 2004/0167668 A1 | 8/2004 | Wang et al. | |
| 2004/0174129 A1* | 9/2004 | Wang et al. | 318/568.12 |
| 2004/0215490 A1 | 10/2004 | Duchon et al. | |
| 2005/0021182 A1 | 1/2005 | Wang et al. | |
| 2005/0021183 A1 | 1/2005 | Wang et al. | |
| 2005/0021187 A1 | 1/2005 | Wang et al. | |
| 2005/0024485 A1 | 2/2005 | Castles et al. | |
| 2005/0027794 A1 | 2/2005 | Decker | |
| 2005/0028221 A1 | 2/2005 | Liu et al. | |
| 2005/0035862 A1 | 2/2005 | Wildman et al. | |
| 2005/0038416 A1 | 2/2005 | Wang et al. | |
| 2005/0052527 A1 | 3/2005 | Remy et al. | |
| 2005/0065438 A1 | 3/2005 | Miller | |
| 2005/0110867 A1 | 5/2005 | Schulz | |
| 2005/0204438 A1 | 9/2005 | Wang et al. | |
| 2006/0047365 A1 | 3/2006 | Ghodoussi et al. | |
| 2006/0064212 A1 | 3/2006 | Thorne | |
| 2006/0095170 A1* | 5/2006 | Yang et al. | 701/23 |
| 2006/0259193 A1 | 11/2006 | Wang et al. | |
| 2007/0067930 A1* | 3/2007 | Garti | 15/1.7 |

FOREIGN PATENT DOCUMENTS

| | | |
|---|---|---|
| EP | 0981905 B1 | 1/2002 |
| JP | 07-257422 A | 10/1995 |
| JP | 08-084328 A | 3/1996 |
| JP | 2000-032319 A | 1/2000 |
| JP | 2002-046088 | 2/2002 |
| JP | 2002-305743 A | 10/2002 |

OTHER PUBLICATIONS

Bar-Cohen et al., Virtual reality robotic telesurgery simulations using MEMICA haptic system, Mar. 5, 2001, Internet, pp. 1-7.

Bauer, Jeffrey C., "Service Robots in Health Care: The Evolution of Mechanical Solutions to Human Resource Problems", Jun. 2003.

Bauer, John et al., "Remote telesurgical mentoring: feasibility and efficicacy", 2000, IEEE, pp. 1-9.

Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.

Brooks, Rodney, Abstracts from Flesh & Machines, How Robots Will Change Us, "Remote Presence", p. 131-147, Feb. 2002.

Celi et al., "The eICU: It's not just telemedicine", Critical Care Medicine, vol. 29, No. 8 (Supplement), Aug. 2001.

Cleary et al., "State of the art in surgical robotics: Clinical applications and technology challenges", Feb. 24, 2002 Internet, pp. 1-26.

CNN, Floating 'droids' to roam space corridors of the future, Jan. 12, 2000, Internet, pp. 1-4.

CNN.com/Technology, Paging R.Robot: Machine helps doctors with patients, Sep. 30, 2003, Internet, 1-3.

Davies, "Robotics in Minimally Invasive Surgery", 1995, Internet, pp. 5/1-5/2.

DiGiorgio, James, "Is Your Emergency Department of the 'Leading Edge'?", 2005, Internet, pp. 1-4.

Elhajj et al., "Supermedia in Internet-based telerobotic operations", 2001, Internet, pp. 1-14.

Goldberg et al., "Collaborative Teleoperation via the Internet", IEEE International Conference on Robotics and Automation, Apr. 2000, San Francisco, California.

Goldman, Lea, "Machine Dreams", Entrepreneurs, Forbes, May 27, 2002.

Gump, Michael D., "Robot Technology Improves VA Pharmacies", 2001, Internet, pp. 1-3.

Harmo et al., "Moving Eye—Interactive Telepresence Over Internet With a Ball Shaped Mobile Robot", 2000.

Hees, William P., "Communications Design for a Remote Presence Robot", Jan. 14, 2002.

F.A. Candelas Herias et al., "Flexible virtual and remote laboratory for teaching Robotics", FORMATEX 2006.

Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.

Johanson, Supporting video-mediated communication over the Internet, Chalmers University of Technology, Dept of Computer Engineering, Gothenburg, Sweden, 2003.

Jouppi, et al., "Mutually-Immersive Audio Telepresence", Audio Engineering Society Convention Paper, presented at 113$^{th}$ Convention Oct. 2002.

Jouppi, Norman P., "First Steps Towards Mutually-Immersive Mobile Telepresence", CSCW '02, Nov. 16-20, 2002, New Orleans LA.

Kanehiro, Fumio et al., Virtual Humanoid Robot Platform to Develop Controllers of Real Humanoid Robots without Porting, 2001,IEEE, pp. 3217-3276.

Lim, Hun-ok et al., Control to Realize Human-like Walking of a Biped Humanoid Robot, IEE 2000, pp. 3271-3276.

Linebarger, John M. et al., "Concurrency Control Mechanisms for Closely Coupled Collaboration in Multithreaded Virtual Environments", Presence, Special Issue on Advances in Collaborative VEs (2004).

Loeb, Gerald, "Virtual Visit: Improving Communication for Those Who Need It Most", 2001.

Mack, "Minimally invasive and robotic surgery", 2001, Internet IEEE, pp. 568-572.

Magne Charge—Smart Power for Electric Vehicles, Internet, Jun. 27, 2002.

Martin, Anya, "Days Ahead", Assisted Living Today, vol. 9, Nov./Dec. 2002, pp. 19-22.

McCardle et al., "The challenge of utilizing new technology in design education", 2000 Internet, pp. 122-127.

Nakajima et al., "A Multimedia Teleteaching System sing an Electronic Whiteboard for Two-Way Communication of Motion Videos and Chalkboards", 1993, IEEE, pp. 436-441.

Ogata et al., "Development of Emotional Communication Robot: WAMOEBA-2r—Esperimental evaluation . . . ", 2000 IEEE, pp. 175-180.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, Eric John, "Personal Tele-Embodiment", Fall 2001.

Paulos, et al. , "Ubiquitous Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Pin et al., "A New Family of Omnidirectional and Holonomic Wheeled Platforms for Mobile Robots", IEEE, vol. 10, No. 4, Aug. 1994.

Roland Piquepaille's Technology Trends, "How new technologies are modifying your way of life", 2003, Internet, pp. 1-2.

Robot Hardware Mobile Robotics Research Group, Edinburgh, "Mobile Robotics Research Group", 2000 Internet, pp. 1-2.

Roy et al., "Towards Personal Service Robots for the Elderly", Internet, Mar. 7, 2002.

Salemi et al, "MILO: Personal robot platform", 2005, Internet, pp. 1-6.

Sandt, Frederic et al., "Perceptions for a Transport Robot in Public Environments", 1997, IROS '97.

Shimoga et al., Touch and force reflection for telepresence surgery, 1994, IEEE, pp. 1049-1050.

Stephenson, Gary, "Dr. Robot Tested at Hopkins", Aug. 5, 2003, Internet, pp. 1-2.

Stoianovici et al., "Robotic Tools for Minimally Invasive Urologic Surgery", Dec. 2002, Internet, 1-17.

Tendick et al., "Human-Machine Interfaces for Minimally Invasive Surgery", 1997, IEEE, pp. 2771-2776.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Urquhart, Kim, "InTouch's robotic Companion 'beams up' healthcare experts", Medical Device Daily, vol. 7, No. 39, Feb. 27, 2003, p. 1, 4.

Weiss et al., Telework and video-mediated communication: Importance of real-time, interactive communication for workers with disabilities, 1999, Internet, pp. 1-4.

Yamasaki et al., Applying Personal Robots and Active Interface to Video Conference Systems, 1995, Internet, pp. 243-248.

Yong et al., "Robot task execution with telepresence using virtual reality technology", 1998, Internet, pp. 1-9.

Zipperer, Lorri, "Robotic dispensing system", 1999, Internet, pp. 1-2.

Zorn, Benjamin G., "Ubiquitous Telepresence", http://www.cs.colorado.edu/~zorn/ut/vision/vision.html, Mar. 5, 1996.

* cited by examiner

GRAPHICAL INTERFACE FOR A REMOTE PRESENCE SYSTEM

BACKGROUND OF THE INVENTION

1. Field of the Invention

The subject matter disclosed generally relates to the field of mobile two-way teleconferencing.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

Tele-robots such as hazardous waste handlers and bomb detectors may contain a camera that allows the operator to view the remote site. Canadian Pat. No. 2289697 issued to Treviranus, et al. discloses a teleconferencing platform that has both a camera and a monitor. The platform includes mechanisms to both pivot and raise the camera and monitor. The Treviranus patent also discloses embodiments with a mobile platform, and different mechanisms to move the camera and the monitor.

There has been marketed a mobile robot introduced by InTouch Technologies, Inc., the assignee of this application, under the trademarks COMPANION and RP-6. The InTouch robot is controlled by a user at a remote station. The remote station may be a personal computer with a joystick that allows the user to remotely control the movement of the robot. Both the robot and the remote station have cameras, monitors, speakers and microphones to allow for two-way video/audio communication.

In the InTouch system, information is sent through a broadband network such as the Internet. Internet access for the control stations of the InTouch system require some type of hardwired interconnect such as a Cablemodem or DSL line. This approach limits the useful area of the control station. It would be desirable to provide a system that allows for the control of a mobile two-way video-conferencing robot from a portable device.

BRIEF SUMMARY OF THE INVENTION

A robot system that includes a portable control station that can be used to control a mobile robot through a cellular network.

DETAILED DESCRIPTION

Disclosed is a robot system that includes a mobile robot and a portable control station that communicate through a cellular network. Utilizing a cellular network allows the control station to be a portable device such as a laptop computer or a personal digital assistant.

Figure 1:
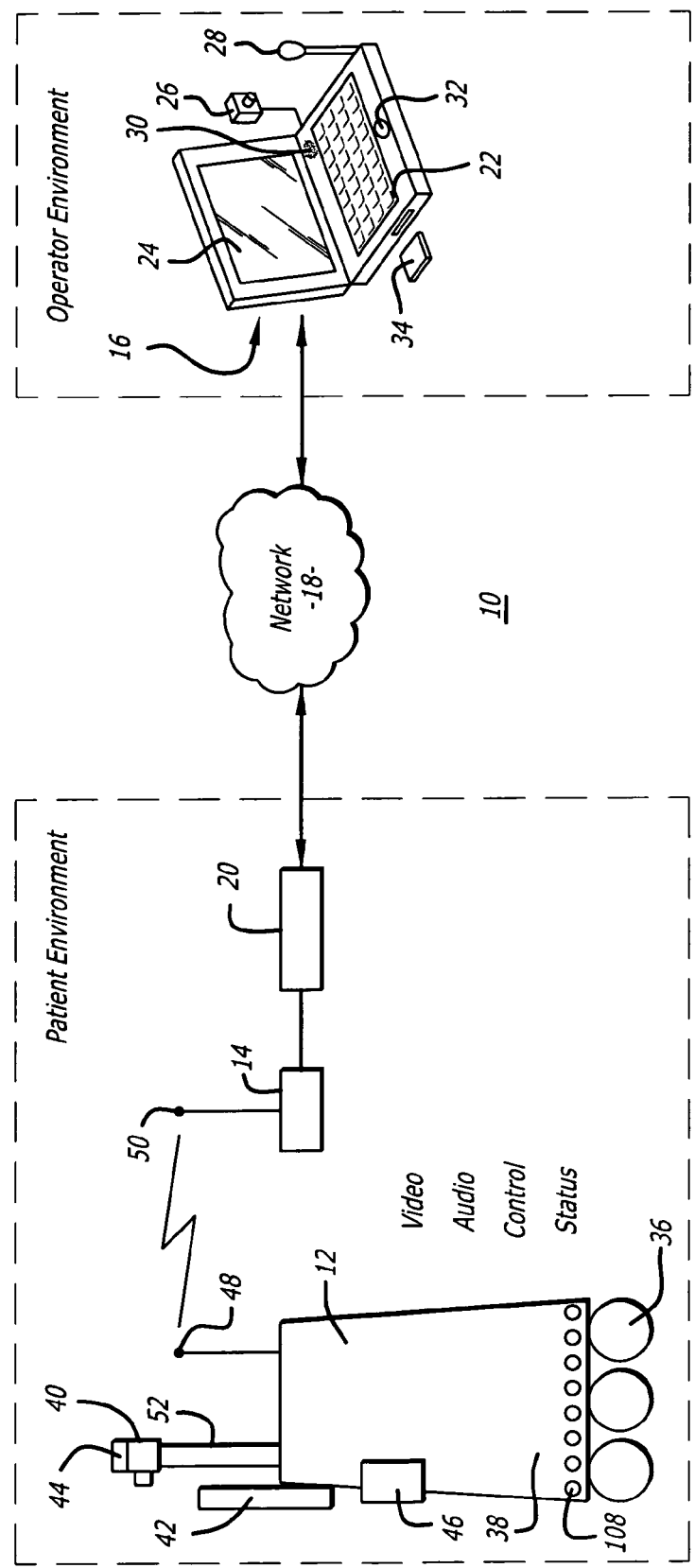
FIG. 1 is an illustration of a robotic system.

Referring to the drawings more particularly by reference numbers, FIG. 1 shows a robot system 10. The robot system includes a robot 12, a base station 14 and a portable control station 16. The portable control station 16 may be coupled to the base station 14 through a cellular network 18. The network 18 may include a wireless network that can send and receive wireless signals in a cellular protocol. The network 18 may also include a broadband network such as the Internet. Utilizing a broadband wireless network 18 allows cellular control signals to be wirelessly transmitted and provided to either the robot or control station in packets. For example, the transmitted information may be packetized in TCP/IP format or a UDP format.

The base station 14 may be coupled to the network 18 by a modem 20 or other broadband network interface device. By way of example, the base station 14 may be a wireless router. Alternatively, the robot 12 may have a direct connection to the network thru for example a satellite.

The portable control station 16 may include a laptop computer 22 that has a screen 24, a camera 26, a microphone 28 and a speaker 30. The camera 26 and microphone 28 may be separate components that are attached to the laptop through an I/O port. The computer 22 may also contain an input device 32 such as a mouse. The control station 16 is typically located in a place that is remote from the robot 12. Although only one portable control station 16 is shown, the system 10 may include a plurality of portable stations. In general any number of robots 12 may be controlled by any number of portable stations 16 or other robots 12. For example, one portable station 16 may be coupled to a plurality of robots 12, or one robot 12 may be coupled to a plurality of control stations 16, or a plurality of robots 12.

The laptop computer 22 may include a wireless network interface card 34 that can transmit and receive wireless signals from the wireless network 18. By way of example, the card 34 by a product sold by Verizon under the name V620.

Each robot 12 includes a movement platform 36 that is attached to a robot housing 38. Also attached to the robot housing 38 are a camera 40, a monitor 42, a microphone(s) 44 and a speaker(s) 46. The microphone 44 and speaker 46 may create a stereophonic sound. The robot 12 may also have an antenna 48 that is wirelessly coupled to an antenna 50 of the base station 14. The system 10 allows a user at the remote control station 16 to move the robot 12 through operation of the input device 32. The robot camera 40 is coupled to the portable station 16 so that a user at the station 16 can view a patient. Likewise, the robot monitor 42 may be coupled to the camera 26 of the computer so that the patient may view the user. The microphones 28 and 44, and speakers 30 and 46, allow for audible communication between the patient and the user. The robotic camera 40 may be mounted to a robotic head 52 that can move the camera 40.

The laptop computer 22 may operate Microsoft OS software and WINDOWS XP or other operating systems such as LINUX. The computer 22 may also operate a video driver, a camera driver, an audio driver and a movie driver. The video images may be transmitted and received with compression software such as MPEG CODEC. The software may be the similar to software provided by InTouch Technologies, Inc. of Santa Barbara, Calif., the assignee of the application, to remotely control mobile robots.

Figure 2:
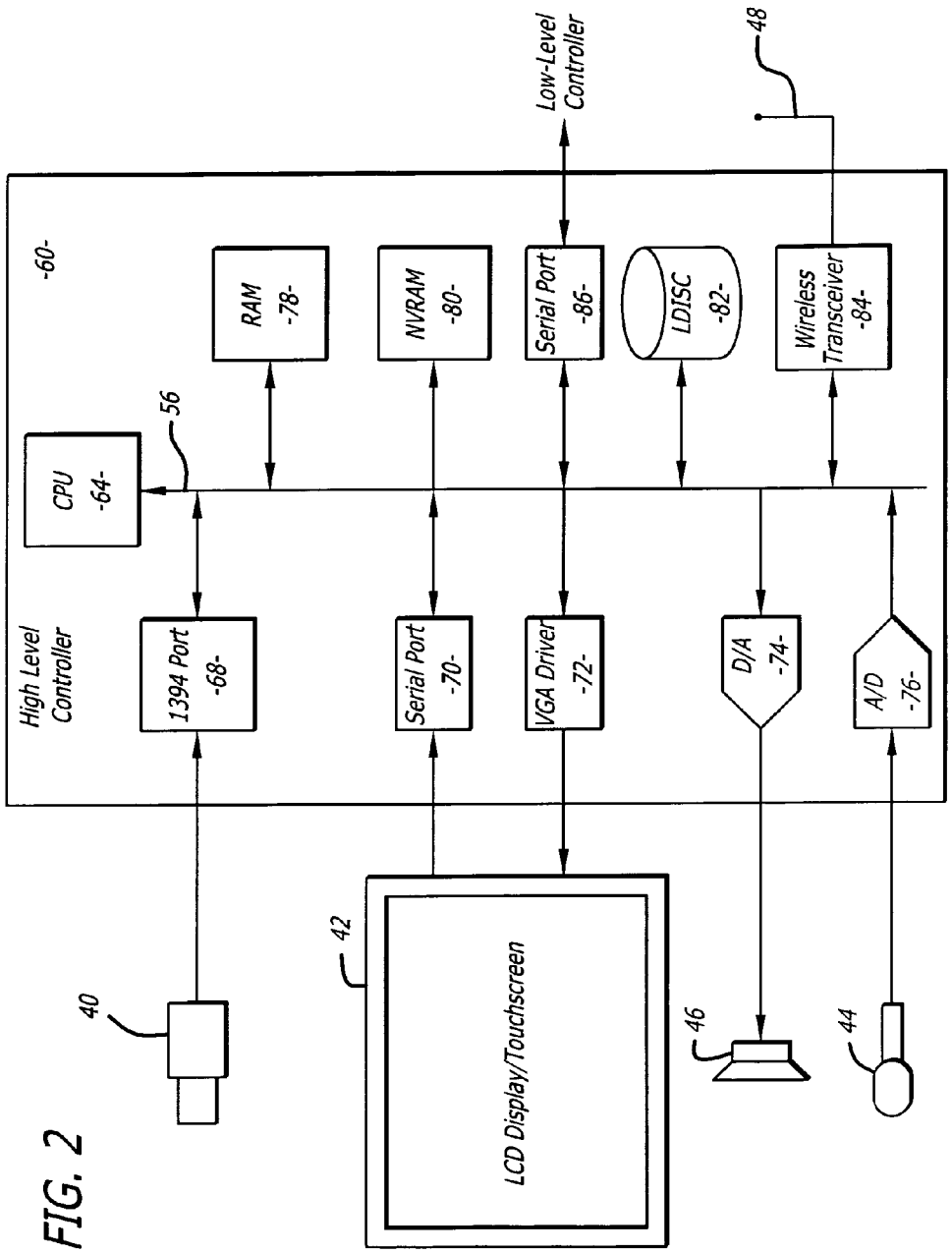
FIG. 2 is a schematic of an electrical system of a robot.
Figure 3:
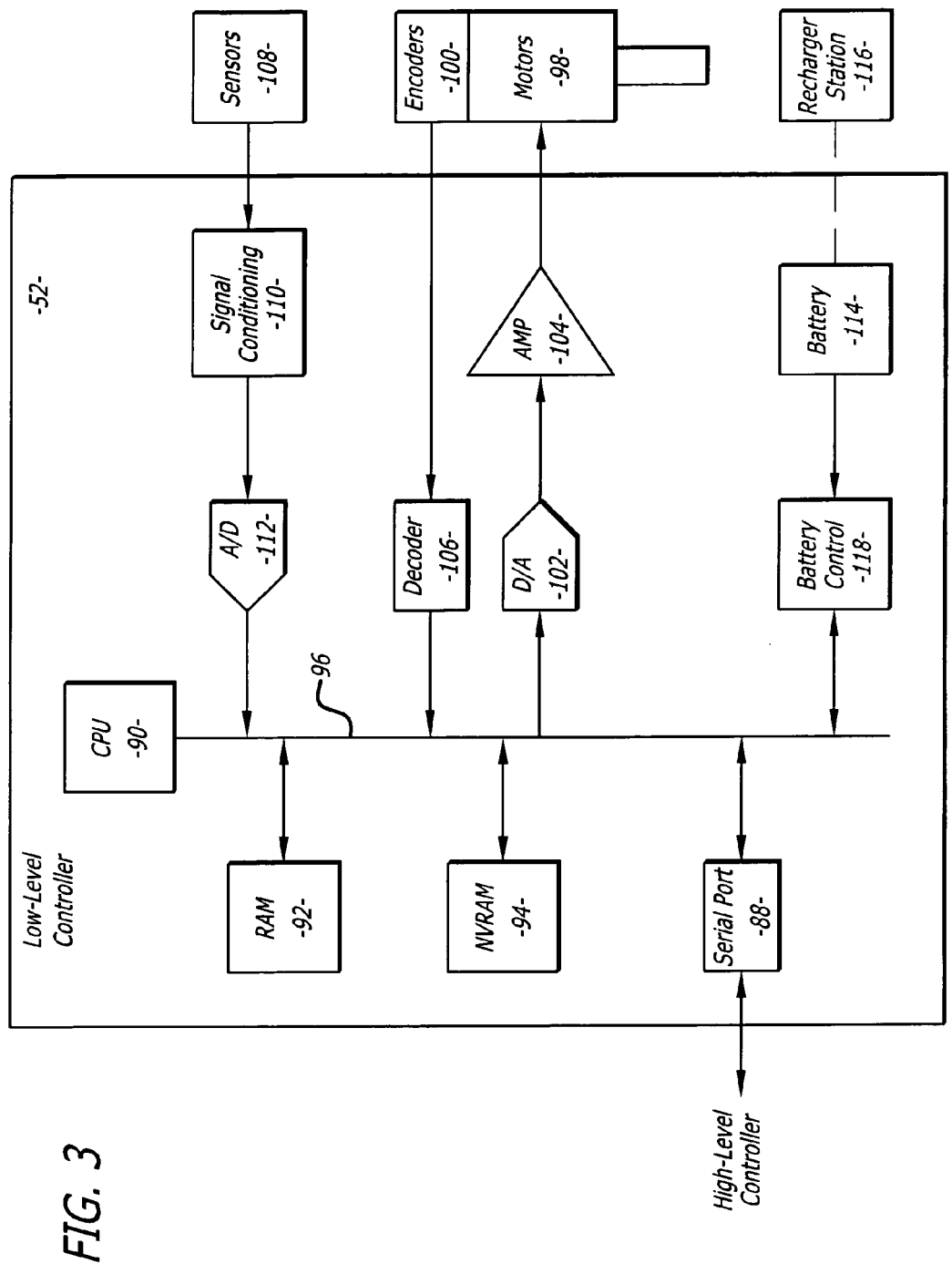
FIG. 3 is a further schematic of the electrical system of the robot.

FIGS. 2 and 3 show an embodiment of a robot 12. Each robot 12 may include a high level control system 60 and a low level control system 62. The high level control system 60 may include a processor 64 that is connected to a bus 66. The bus is coupled to the camera 38 by an input/output (I/O) port 68, and to the monitor 42 by a serial output port 70 and a VGA driver 72. The monitor 42 may include a touchscreen function that allows the patient to enter input by touching the monitor screen.

The speaker 46 is coupled to the bus 66 by a digital to analog converter 74. The microphone 44 is coupled to the bus 66 by an analog to digital converter 76. The high level controller 60 may also contain random access memory (RAM) device 78, a non-volatile RAM device 80 and a mass storage device 82 that are all coupled to the bus 72. The mass storage device 82 may contain medical files of the patient that can be accessed by the user at the remote control station 16. For example, the mass storage device 82 may contain a picture of the patient. The user, particularly a health care provider, can recall the old picture and make a side by side comparison on the monitor 24 with a present video image of the patient provided by the camera 38. The robot antennae 48 may be coupled to a wireless transceiver 84. By way of example, the transceiver 84 may transmit and receive information in accordance with IEEE 802.11b.

The controller 64 may operate with a LINUX OS operating system. The controller 64 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 60 operates to control communication between the robot 12 and the remote control station 16.

The high level controller 60 may be linked to the low level controller 62 by serial ports 86 and 88. The low level controller 62 includes a processor 90 that is coupled to a RAM device 92 and non-volatile RAM device 94 by a bus 96. Each robot 12 contains a plurality of motors 98 and motor encoders 100. The motors 98 can activate the movement platform and move other parts of the robot such as the monitor and camera. The encoders 100 provide feedback information regarding the output of the motors 98. The motors 98 can be coupled to the bus 96 by a digital to analog converter 102 and a driver amplifier 104. The encoders 100 can be coupled to the bus 96 by a decoder 106. Each robot 12 also has a number of proximity sensors 108 (see also FIG. 1). The position sensors 108 can be coupled to the bus 96 by a signal conditioning circuit 110 and an analog to digital converter 112.

The low level controller 62 runs software routines that mechanically actuate the robot 12. For example, the low level controller 62 provides instructions to actuate the movement platform to move the robot 12. The low level controller 62 may receive movement instructions from the high level controller 60. The movement instructions may be received as movement commands from the remote control station or another robot. Although two controllers are shown, it is to be understood that each robot 12 may have one controller, or more than two controllers, controlling the high and low level functions.

The various electrical devices of each robot 12 may be powered by a battery(ies) 114. The battery 114 may be recharged by a battery recharger station 116. The low level controller 62 may include a battery control circuit 118 that senses the power level of the battery 114. The low level controller 62 can sense when the power falls below a threshold and then send a message to the high level controller 60.

The system may be the same or similar to a robotic system provided by the assignee InTouch Technologies, Inc. of Santa Barbara, California under the name RP-6, which is hereby incorporated by reference. The system may also be the same or similar to the system disclosed in Vis, U.S. Pat. No. 6,925, 357, which is hereby incorporated by reference.

Figure 4:
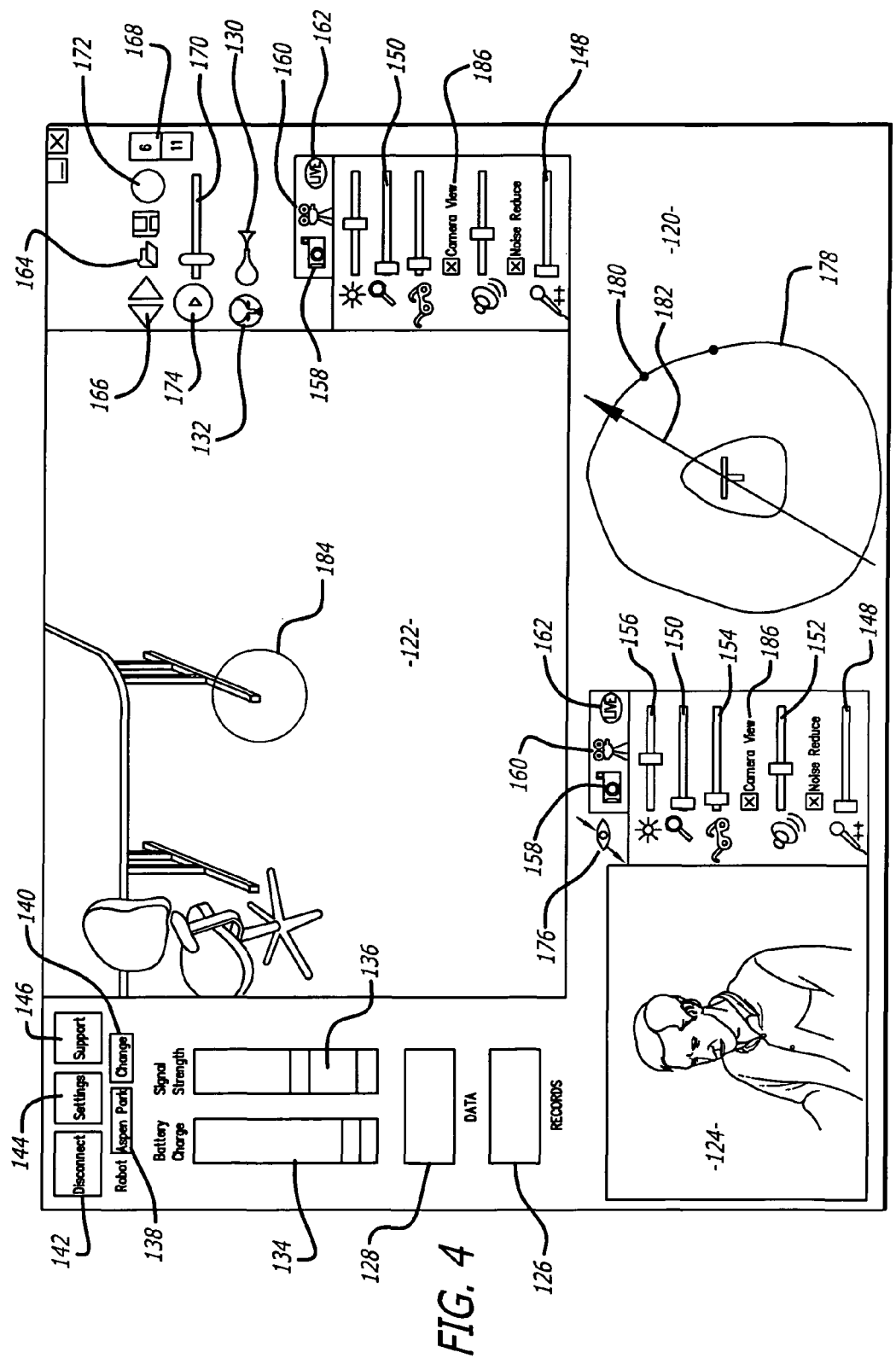
FIG. 4 is a display user interface of a remote station.

FIG. 4 shows a display user interface ("DUI") 120 that can be displayed by the screen 24 of the computer 22 and/or the robot 12. The DUI 120 may include a robot view field 122 that displays a video image captured by the camera of the robot. The DUI 120 may also include a station view field 124 that displays a video image provided by the camera 26 of the control station 16. The DUI 120 may be part of an application program stored and operated by the computer 22 of the control station 16.

Figure 5:
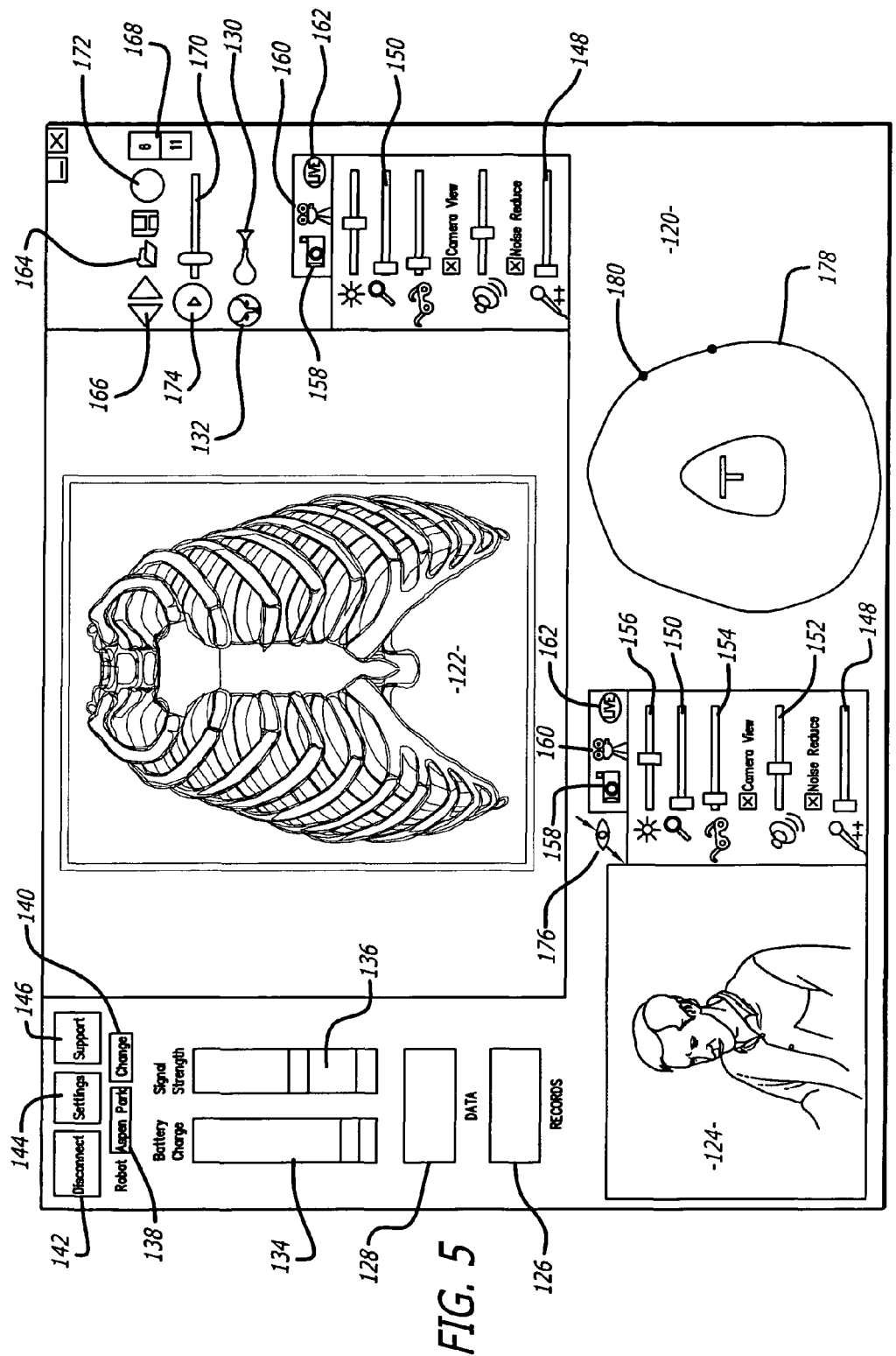
FIG. 5 is a display user interface showing an electronic medical record.
Figure 6:
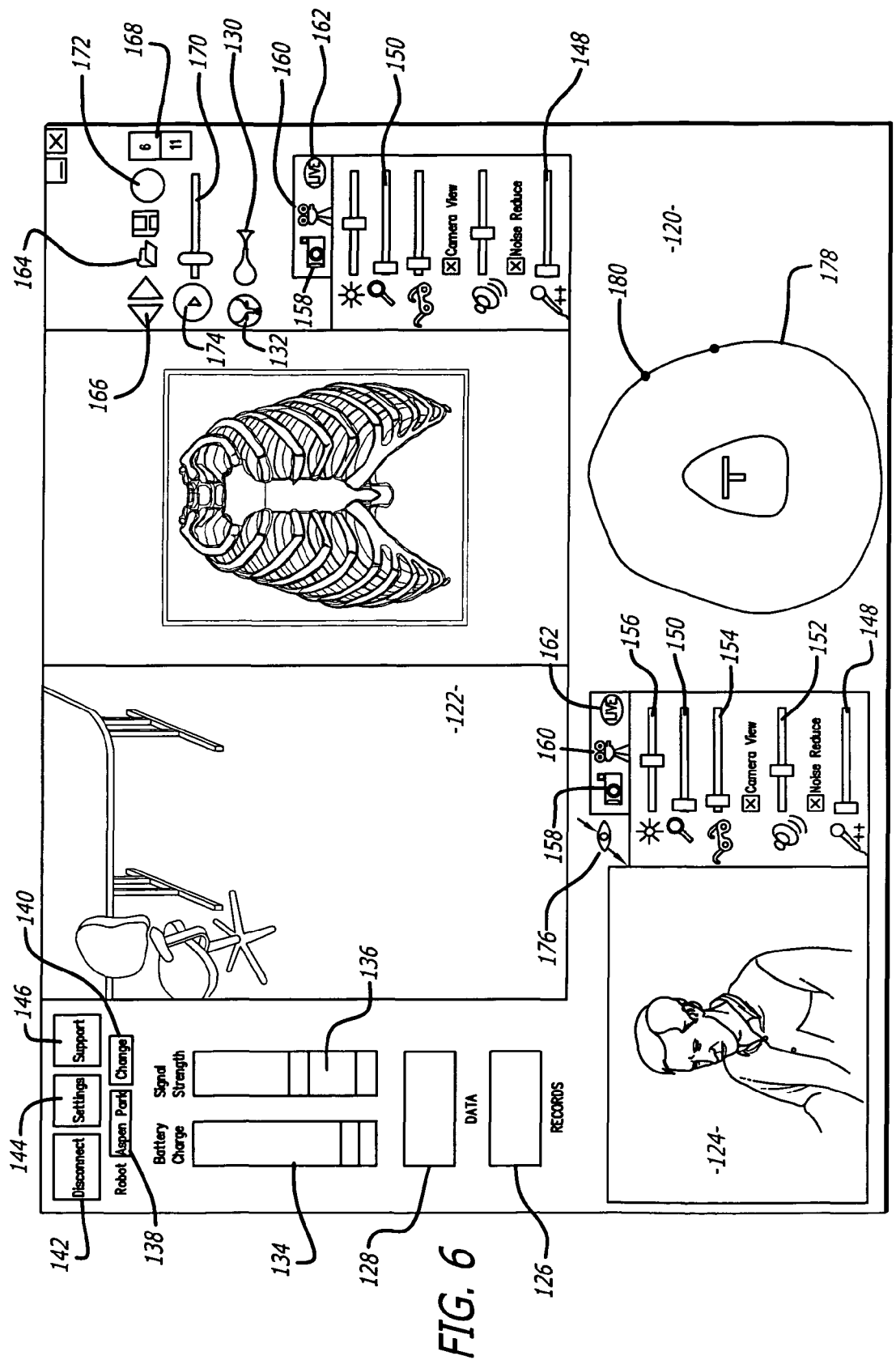
FIG. 6 is a display user interface showing an image and an electronic medical record being simultaneously displayed.

The DUI 120 may include a graphic button 126 that can be selected to display an electronic medical record as shown in FIG. 5. The button 126 can be toggled to sequentially view the video image and the electronic medical record. Alternatively, the view field 122 may be split to simultaneously display both the video image and the electronic medical record as shown in FIG. 6. The viewing field may allow the physician to modify the medical record by adding, changing or deleting all or part of the record. The remote clinician can also add to the medical record still images or video captured by the camera of the robot. Although a medical record is shown and described, it is to be understood that any information that can be shown on the screen 24 can be stored and displayed.

The DUI 120 may have a monitor data field 128 that can display the data generated by the medical monitoring device (s) and transmitted to the control station. The data can be added to the electronic medical record, either automatically or through user input. For example, the data can be added to a record by "dragging" a monitor data field 128 into the viewing field 122.

The DUI 120 may include alert input icons 130 and 132. Alert icon 130 can be selected by the user at the control station to generate an alert indicator such as a sound from the speaker of the robot. Selection of the icon generates an alert input to the robot. The robot generates a sound through its speaker in response to the alert input. By way of example, the sound may simulate the noise of a horn. Consequently, the icon may have the appearance of a horn. The remote station user may select the horn shaped icon 130 while remotely moving the robot to alert persons to the presence of the moving robot.

Alert icon 132 can be selected to request access to the video images from the robot. The default state of the robot may be to not send video information to the remote station. Selecting the alert icon 132 sends an alert input such as an access request to the robot. The robot then generates an alert indicator. The alert indicator can be a sound generated by the robot speaker, and/or a visual prompt on the robot monitor. By way of example, the visual prompt may be a "flashing" graphical icon. The sound may simulate the knocking of a door. Consequently, the alert icon 132 may have the appearance of a door knocker.

In response to the alert indicator the user may provide a user input such as the depression of a button on the robot, or the selection of a graphical image on the robot monitor, to allow access to the robot camera. The robot may also have a voice recognition system that allows the user to grant access with a voice command. The user input causes the robot to begin transmitting video images from the robot camera to the control station that requested access to the robot. A voice communication may be established before the cycle of the alert input and response, to allow the user at the control station to talk to the caller recipient at the robot.

The DUI 120 may include a graphical "battery meter" 134 that indicates the amount of energy left in the robot battery. A graphical "signal strength meter" 136 may indicate the strength of the wireless signal transmitted between the robot and the base station (see FIG. 1).

The DUI 120 may include a location display 138 that provides the location of the robot. The CHANGE button 140 can be selected to change the default robot in a new session. The CHANGE button 140 can be used to select and control a different robot in a system that has multiple robots. The user can initiate and terminate a session by selecting box 142. The box 142 changes from CONNECT to DISCONNECT when the user selects the box to initiate a session. System settings and support can be selected through buttons 144 and 146.

Both the robot view field 122 and the station view field 124 may have associated graphics to vary the video and audio displays. Each field may have an associated graphical audio slide bar 148 to vary the audio level of the microphone and another slide bar 152 to vary the volume of the speakers.

The DUI 120 may have slide bars 150, 154 and 156 to vary the zoom, focus and brightness of the cameras, respectively. A still picture may be taken at either the robot or remote station by selecting one of the graphical camera icons 158. The still picture may be the image presented at the corresponding field 122 or 124 at the time the camera icon 158 is selected. Capturing and playing back video can be taken through graphical icons 160. A return to real time video can be resumed, after the taking of a still picture, captured video, or reviewing a slide show, by selecting a graphical LIVE button 162.

A still picture can be loaded from disk for viewing through selection of icon 164. Stored still images can be reviewed by selecting buttons 166. The number of the image displayed relative to the total number of images is shown by graphical boxes 168. The user can rapidly move through the still images in a slide show fashion or move through a captured video clip by moving the slide bar 170. A captured video image can be paused through the selection of circle 174. Play can be resumed through the same button 174. Video or still images may be dismissed from the active list through button 172. Video or still images may be transferred to the robot by selecting icon 176. For example, a doctor at the remote station may transfer an x-ray to the screen of the robot.

A graphical depiction of the base of the robot can be shown in sensor field 178. The sensor may have various sensors that sense contact with another object. The sensor field 178 can provide a visual display of the sensors that detect the object. By way of example, the field may have one or more graphical dots 180 that display where on the robot the sensors detected an object. This provides the user with a sense of the robot environment that is outside the view of the robot camera.

The graphical depiction of the robot base may contain a graphical vector overlay 182 that indicates the direction of robot movement. The direction of movement may be different than the direction the camera is facing. The vector can provide a visual aid when driving the robot.

The system may provide the ability to annotate 184 the image displayed in field 122 and/or 124. For example, a doctor at the remote station may annotate some portion of the image captured by the robot camera. The annotated image may be stored by the system. The system may also allow for annotation of images sent to the robot through icon 176. For example, a doctor may send an x-ray to the robot which is displayed by the robot screen. The doctor can annotate the x-ray to point out a portion of the x-ray to personnel located at the robot site. This can assist in allowing the doctor to instruct personnel at the robot site.

The display user interface may include graphical inputs 186 that allow the operator to turn the views of the remote station and remote cameras on and off.

Figure 7:
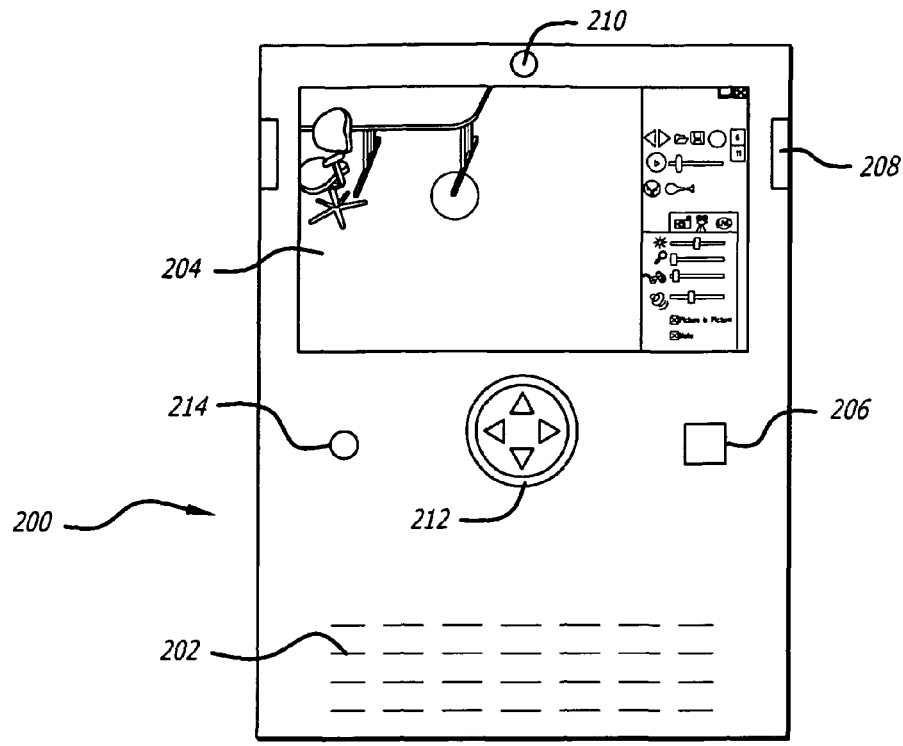
FIG. 7 is an illustration of a PDA control station.

As shown in FIG. 7 the portable control station may be a personal digital assistant ("PDA") 200. The PDA 200 includes a keypad 202 and a screen 204. The PDA 200 may also include a microphone 206, a speaker 208 and a camera 210. Given the relatively small size of the screen 204 the PDA may display only the robot field 122 and associated graphic buttons 150, 160, etc. shown in FIG. 4. The PDA 200 may provide a menu so that the screen 204 can display fields 120 and 124 and also the system data such as signal strength 136, etc.

Figures 8A, 8B, 8C:
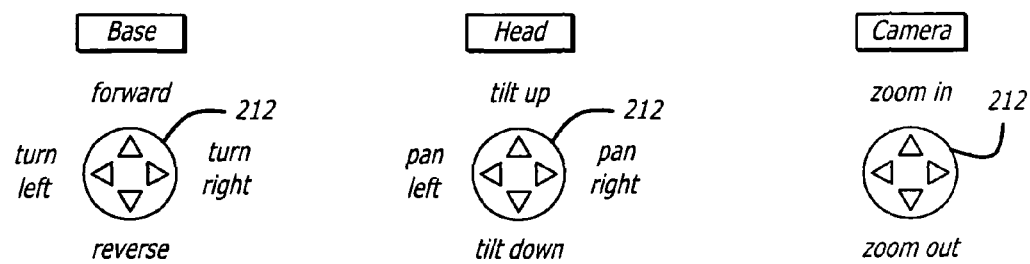
FIGS. 8A-C are illustrations of a control button that can be placed into a plurality of modes.

The PDA 200 may have a button, or buttons, 212 to perform various control functions of the mobile robot. The mode of the button 212 can be controlled through a mode button 214. The different modes are shown in FIGS. 8A, B and C. In one mode, shown in FIG. 8A, the button 212 can be used to turn the mobile platform of the robot. This allows the user to control the movement of the robot. For example, the user can move the robot forward by pushing the top of the button 212, or left by pushing the left side of the button 212. FIG. 8B shows a second mode wherein the user can control the movement of the camera head. For example, the camera can be tilted downward by pushing the bottom portion of the button 212. A third mode for controlling a zoom function of the camera is shown in FIG. 8C. By way of example, the user can zoom out by pushing the bottom of the button 212, or zoom in by pushing the top of the button 212.

The PDA 200 may be operated through a stylus (now shown) that allows a user to make selections by touching a screen. Additionally, the control icons may not always be displayed with the video image. The video image may be displayed with a single "pop-up" icon that can be selected to pull up the control options, such as the graphical buttons.

By way of example, the PDA may be a device sold by Hewlett Packard under the product name ipPAQ x2795, although it is to be understood that other types of products can be utilized in the system 10. Alternatively, the portable control station may be a cellular phone with the functions of a PDA.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robot system, comprising:
   a mobile robot that has a mobile base and a head that moves a monitor and a camera that captures an image; and,
   a portable control station that is coupled to said mobile robot to receive and display said captured image, said portable control station includes a single input that allows a user to select one of a plurality of different modes, one of said modes allows a user to move said robot base through said single input and another mode allows the user to move said robot head through said single input.

2. The system of claim 1, wherein said portable control station includes a laptop computer.

3. The system of claim 1, wherein said portable control station includes a personal digital assistant.

4. The system of claim 1, wherein said mobile robot includes a mobile platform and a camera head, said portable control station includes an input that can be used to control said mobile platform and said camera head with a single finger.

5. The system of claim 1, wherein said mobile robot includes a microphone, a speaker and a monitor, said portable control station includes one or more graphical user interfaces with selectable inputs to vary parameters of said mobile robot.

6. The system of claim 1, wherein said portable control station includes a microphone, a speaker and a monitor, said portable control station includes one or more graphical user interfaces with selectable inputs to vary parameters of said mobile robot.

7. The system of claim 1, further comprising a base station that is coupled to said portable control station and wirelessly coupled to said mobile robot.

8. The system of claim 1, wherein said portable control station includes a cellular transceiver card.

9. The system of claim 1, wherein said portable control station includes a graphical user interface that allows a user to select one or more of a plurality of fields that are displayed by said portable control station.

10. A robot system, comprising:

a cellular network;

a mobile robot that is coupled to said cellular network and has a mobile base and a head that moves a monitor and a camera that captures an image; and, a portable control station that is coupled to said cellular network and said mobile robot to receive and display said captured image, said portable control station transmits a plurality of cellular signals through said cellular network that control movement of said mobile robot, said mobile robot, said portable control station includes a single input that allows a user to select one of a plurality of different modes, one of said modes allows a user to move said robot base through said single input and another mode allows the user to move said robot head through said single input.

11. The system of claim 10, wherein said portable control station includes a laptop computer.

12. The system of claim 10, wherein said portable control station includes a personal digital assistant.

13. The system of claim 10, wherein said mobile robot includes a mobile platform and a camera head, said portable control station includes an input that can be used to control said mobile platform and said camera head with a single finger.

14. The system of claim 10, wherein said mobile robot includes a microphone, a speaker and a monitor, said portable control station includes one or more graphical user interfaces with selectable inputs to vary parameters of said mobile robot.

15. The system of claim 10, wherein said portable control station includes a microphone, a speaker and a monitor, said portable control station includes one or more graphical user interfaces with selectable inputs to vary parameters of said mobile robot.

16. The system of claim 10, further comprising a base station that is coupled to said portable control station and wirelessly coupled to said mobile robot.

17. The system of claim 10, wherein said portable control station includes a cellular transceiver card.

18. The system of claim 10, wherein said portable control station includes a graphical user interface that allows a user to select one or more of a plurality of fields that are displayed by said portable control station.

19. A method for operating a robot, comprising:

transmitting a plurality of signals through a network from a portable control station to a mobile robot, the mobile robot has a mobile base and a head that moves a monitor and a head;

moving the mobile robot in response to the signals;

transmitting an image captured by the camera of the mobile robot to the portable control station through the cellular network;

displaying the image at the portable control station;

changing a mode through a single input to enter a base mode;

inputting commands through the single input to move the robot base;

changing the mode through the single input to enter a head mode; and, inputting commands through the single input to move the robot head.

20. The method of claim 19, wherein the plurality of signals contain information in TCP/IP format.

* * * * *